United States Patent
Shalaby et al.

(10) Patent No.: US 8,927,001 B2
(45) Date of Patent: Jan. 6, 2015

(54) BIOSWELLABLE, CRYSTALLINE, AMPHIPHILIC, BLOCK/GRAFT POLYMERS AND APPLICATIONS THEREOF

(75) Inventors: Shalaby W. Shalaby, Anderson, SC (US); James M. Lindsey, Pendleton, SC (US)

(73) Assignee: Poly-Med, Inc., Anderson, SC (US)

( * ) Notice: Subject to any disclaimer, the term of this patent is extended or adjusted under 35 U.S.C. 154(b) by 1279 days.

(21) Appl. No.: 11/453,207

(22) Filed: Jun. 14, 2006

(65) Prior Publication Data

US 2006/0286143 A1   Dec. 21, 2006

Related U.S. Application Data

(60) Provisional application No. 60/690,751, filed on Jun. 15, 2005.

(51) Int. Cl.
    *A61F 2/02*     (2006.01)
    *C08F 8/30*    (2006.01)
    *A61L 31/06*   (2006.01)
    *A61L 17/14*   (2006.01)
    *A61L 27/34*   (2006.01)
    *A61L 29/08*   (2006.01)
    *A61L 31/10*   (2006.01)

(52) U.S. Cl.
    CPC .............. *A61L 17/145* (2013.01); *A61L 27/34* (2013.01); *A61L 29/085* (2013.01); *A61L 31/10* (2013.01)
    USPC .......................................... 424/423; 525/127

(58) Field of Classification Search
    None
    See application file for complete search history.

(56) References Cited

U.S. PATENT DOCUMENTS

| | | | |
|---|---|---|---|
| 4,624,256 A | 11/1986 | Messier | |
| 4,857,602 A | 8/1989 | Casey et al. | |
| 5,123,912 A | 6/1992 | Kaplan | |
| 5,320,624 A | 6/1994 | Kaplan | |
| 5,352,515 A * | 10/1994 | Jarrett et al. | 428/357 |
| 5,543,158 A | 8/1996 | Gref | |
| 5,612,052 A | 3/1997 | Shalaby | |
| 5,702,711 A | 12/1997 | Parab | |
| 5,714,159 A | 2/1998 | Shalaby | |
| 6,136,018 A | 10/2000 | Roby | |
| 6,485,749 B1 | 11/2002 | Shalaby | |
| 6,498,229 B1 * | 12/2002 | Shalaby | 528/302 |
| 2001/0000728 A1 * | 5/2001 | Sawhney et al. | 424/78.08 |
| 2003/0162894 A1 * | 8/2003 | Buchholz et al. | 525/53 |
| 2003/0162940 A1 * | 8/2003 | Shalaby | 528/425 |
| 2004/0167575 A1 | 8/2004 | Roby | |
| 2005/0038472 A1 | 2/2005 | Furst | |
| 2005/0171299 A1 | 8/2005 | Shalaby | |

OTHER PUBLICATIONS

Shalaby et al., Water Soluble Polymers, Chapter 30, Amercian Chemical Society, Washington, 1991, p. 482.

Peppas, Hydrogels in Medicine and Pharmacy, vol. 1, CRC Press, 1986, p. 2.

Park et al., Biodegradable Hydrogels for Drug Delivery, Chapter 1, Technomic Publishing Co., 1993, pp. 1-2.

Cai et al., Synthesis and properties of ABA-type triblock copolymers of poly(glycolide-o-caprolactone) (A) and poly(ethylene glycol (B), Polymer 43, p. 3585-3591, 2002.

* cited by examiner

*Primary Examiner* — Scott Long
*Assistant Examiner* — Sarah Alawadi
(74) *Attorney, Agent, or Firm* — Douglas L. Lineberry

(57) ABSTRACT

Absorbable, essentially non-absorbable, and non-absorbable crystalline, amphiphilic, block/graft copolymeric compositions exhibit an inherent viscosity of at least 0.5 dL/g, a heat of fusion of at least 10 J/g and undergo swelling in the biological environment due to a water up-take of at least 10 percent of original dry mass. These compositions are designed for use in swellable surgical sutures, coatings of medical devices, and carriers for the delivery of bioactive agents.

10 Claims, No Drawings

BIOSWELLABLE, CRYSTALLINE, AMPHIPHILIC, BLOCK/GRAFT POLYMERS AND APPLICATIONS THEREOF

The present application claims the benefit of prior provisional application U.S. Ser. No. 60/690,751, filed Jun. 15, 2005.

FIELD OF THE INVENTION

This invention is directed toward structurally tailored high molecular weight, absorbable, essentially non-absorbable, and non-absorbable crystalline, amphiphilic block/graft copolymeric compositions comprising highly hydrophilic and relatively hydrophobic blocks/grafts, or components for use as surgical sutures, carriers for the delivery of bioactive agents, or coatings of medical devices, which display an inherent viscosity of at least 0.5 dL/g, heat of fusion of at least 10 J/g and are capable of absorbing at least 10 percent of their original dry mass when present in the biological environment. These compositions can be used for the production of swellable sutures, coatings of medical devices, and carriers for the delivery of bioactive agents. The sutures and coating are designed to undergo absorption in the biological environment within a three-year period or to be essentially non-absorbable during this period. The swellable coatings can be used as absorbable or essentially non-absorbable material, capable of space filing for devices used to treat vascular aneurysm. The swellable sutures, whether absorbable or essentially non-absorbable, can be used in surgical procedures to minimize or eliminate blood leakage through needle-punctured tissue, or needle-imparted holes, particularly in procedures associated with the cardiovascular system.

BACKGROUND OF THE INVENTION

It is widely acknowledged that swellable synthetic polymers can be obtained through the covalent crosslinking of water-soluble polymers to form three-dimensional networks, yielding, in most cases, what is known in the industry as the precursors of hydrogels [Chapter 30 in *Water Soluble Polymers* (Shalaby, S. W. et al., Eds.), American Chemical Society, Washington, 1991, p. 482; Chapter II in *Hydrogels in Medicine and Pharmacy*, Vol. I (Peppas, N. A., Ed.), CRC Press, 1986, p. 2; and Chapter 1 in *Biodegradable Hydrogels for Drug Delivery* (Park, K et al.), Technomic Publishing Co., 1993, pps. 1 and 2].

A concise outline dealing with water-swellable polymer networks and related systems is available through the Sigma-Aldrich web site (www.Sigma-Aldrich.com). A paraphrased excerpt of this outline is provided below.

Hydrogels are characterized by the pronounced affinity of their chemical structures for aqueous solutions in which they swell rather than dissolve. Such polymeric networks may range from being mildly absorbing, typically retaining 30 wt. % of water within their structure, to superabsorbing, where they retain many times their weight of aqueous fluids. Several synthetic strategies have been proposed to prepare absorbent polymers: (a) polyelectrolyte(s) subjected to covalent cross-linking; (b) associative polymers consisting of hydrophilic and hydrophobic components ("effective" cross-links through hydrogen bonding); and (c) physically interpenetrating polymer networks yielding absorbent polymers of high mechanical strength. Specific descriptions of major hydrogel precursors are given below:

| Absorbent Polymer | Morphology | Absorption Characteristics |
|---|---|---|
| 1. Poly(acrylic acid), potassium salt, lightly crosslinked | Powder; particle size 99% <1,000 μm | Absorbs ca. 27 g/g of 1% saline solution; rate of absorption more rapid than for corresponding Na salt |
| 2. Poly(acrylic acid), sodium salt, lightly crosslinked | Powder; particle size 99% <1,000 μm | Absorbs ca. 45 g/g of 1% saline solution |
| 3. Poly(acrylic acid-co-acrylamide), potassium salt, crosslinked | Granules; 200–1,000 μm; pH 5.5–6.0 | Absorbs many times its weight of aqueous fluids |
| 4. Poly(acrylic acid, sodium salt-graft-poly(ethylene oxide), crosslinked | Granular powder; 100–850 μm | Absorbs many times its weight of aqueous fluids |
| 5. Poly(2-hydroxyethyl methacrylate), average $M_v$ ca. 300,000 | Crystals | — |
| 6. Poly(2-hydroxypropyl methacrylate) | Crystals | — |
| 7. Poly(isobutylene-co-maleic acid), sodium salt, crosslinked | Fiber; 24–40 μm diameter | Absorption of 0.9 wt % saline solution is ca. 65 g/g; absorption of distilled water is ca. 300 g/g |

(See the Sigma-Aldrich website: www.Sigma-Aldrich.com)

The concept of using amphiphilic, copolyesters with chain molecules comprising covalently linked hydrophilic and hydrophobic segments/blocks to produce swellable polymeric materials or hydrogels through association of the hydrophobic segments and formation of non-covalent, pseudo-crosslinks in the presence of water has been disclosed by Shalaby in U.S. Pat. Nos. 5,612,052 and 5,714,159. However, these amphiphilic copolyesters were described as hydrogel-forming liquids and lack needed properties to form solid, swellable products such as those needed in producing surgical implants, coatings of surgical implants or carriers for the delivery of bioactive agents, requiring different levels of structural integrity, which cannot be provided by the hydrogel-forming liquids. Other inventors have also disclosed the use of amphiphilic copolymers comprising polyethylene glycol interlinked with polyester as carriers for the delivery of bioactive agents [U.S. Pat. No. 5,702,711]. However, all these polymers were designed to be water-soluble materials that swell and undergo dissolution and lose their mechanical integrity. The above cited prior art and contemporary needs for swellable, space-filling implants and coatings as well as drug carriers with modulated swelling profiles provided an incentive to explore the subject of the present invention.

SUMMARY OF THE INVENTION

This invention is generally directed to a bioswellable, high molecular weight, crystalline, amphiphilic, block/graft copolymeric composition comprising a hydrophilic component covalently linked to a crystalline hydrophobic component wherein said composition exhibits an inherent viscosity of at least 0.5 dL/g, heat of fusion of at least 10 J/g and is capable of absorbing at least 10% of its dry mass of water when present in the biological environment, wherein both the hydrophilic and hydrophobic components are crystalline with the hydrophilic component comprising a polyethylene oxide central block and the hydrophobic component comprising two terminal blocks comprising repeat units arising from at least one cyclic monomer selected from the group represented by ε-caprolactone, p-dioxanone, glycolide, l-lactide, trimethylene carbonate, and a morpholinedione. Additionally, these compositions can be used clinically in the form of a swellable (a) surgical suture; (b) a coating for devices used in treating vascular aneurysm; and (c) a carrier for the delivery of at least one bioactive agent.

In another aspect of the present invention is directed to a bioswellable, high molecular weight, crystalline, amphiphilic, block/graft copolymeric composition comprising a hydrophilic component covalently linked to a crystalline hydrophobic component wherein said composition exhibits an inherent viscosity of at least 0.5 dL/g, heat of fusion of at least 10 J/g and is capable of absorbing at least 10% of its dry mass of water when present in the biological environment wherein the hydrophilic component is non-crystalline and the hydrophobic component is crystalline with the hydrophilic component comprising a polyvinyl pyrrolidone block/graft and the hydrophobic component comprising a polyester chain comprising repeat units arising from one or more cyclic monomer selected from the group represented by ε-caprolactone, p-dioxanone, glycolide, l-lactide, trimethylene carbonate, and a morpholinedione. Furthermore, these compositions can be used clinically in the form of surgical sutures, a coating for a medical device used in treating vascular aneurysm, and a carrier for the delivery of at least one bioactive agent.

Another aspect of this invention deals with a bioswellable, high molecular weight, crystalline, amphiphilic, block/graft copolymeric composition comprising a hydrophilic component covalently linked to a crystalline hydrophobic component wherein said composition exhibits an inherent viscosity of at least 0.5 dL/g, heat of fusion of at least 10 J/g and is capable of absorbing at least 10% of its dry mass of water when present in the biological environment, wherein both the hydrophilic and hydrophobic components are crystalline with the hydrophilic component comprising a polyethylene oxide central block and the hydrophobic component comprising two terminal blocks comprising repeat units arising from at least one cyclic monomer selected from the group represented by ε-caprolactone, p-dioxanone, glycolide, l-lactide, trimethylene carbonate, and a morpholinedione. In these compositions, the hydrophobic and hydrophilic components are interlinked through a flexible chain segment wherein the flexible chain segment comprising repeat units derive from at least one cyclic monomer selected from the group 1,5-dioxepane-2-one, trimethylene carbonate, and ε-caprolactone. Furthermore, these compositions can be used clinically in the form of a surgical suture, coating for a medical device used in treating vascular aneurysm, and carrier for the delivery of at least one bioactive agent.

A special aspect of this invention deals with a bioswellable, high molecular weight, crystalline, amphiphilic, block/graft copolymeric composition comprising a hydrophilic component covalently linked to a crystalline hydrophobic component, the composition having an inherent viscosity of at least 0.5 dL/g, heat of fusion of at least 10 J/g and is capable of absorbing at least 10% of its dry mass of water when present in the biological environment, wherein the hydrophilic block is a diisocyanate-interlinked polyethylene glycol and the hydrophobic block component comprising repeat units arising from at least one cyclic monomer selected from the group consisting of ε-caprolactone, p-dioxanone, glycolide, l-lactide, trimethylene carbonate and a morpholinedione.

A specific aspect of this invention deals with a bioswellable, high molecular weight, crystalline, amphiphilic, block/graft copolymeric composition comprising a hydrophilic component covalently linked to a crystalline hydrophobic component wherein said composition exhibits an inherent viscosity of at least 0.5 dL/g, heat of fusion of at least 10 J/g and is capable of absorbing at least 10% of its dry mass of water when present in the biological environment, wherein the hydrophilic component is non-crystalline and the hydrophobic component is crystalline with the hydrophilic component comprising a polyvinyl pyrrolidone block/graft and the hydrophobic component comprising a polyester chain comprising repeat units arising from one or more cyclic monomer selected from the group represented by ε-caprolactone, p-dioxanone, glycolide, l-lactide, trimethylene carbonate, and a morpholinedione. It is preferred that the hydrophobic and hydrophilic components are interlinked through a flexible chain segment. Furthermore, these compositions can be used clinically in the form of a carrier for the delivery of at least one bioactive agent.

DETAILED DESCRIPTION OF PREFERRED EMBODIMENTS

This invention is generally directed to structurally tailored, high molecular weight, crystalline amphiphilic block/graft absorbable, essentially non-absorbable, and non absorbable copolymeric compositions exhibiting an inherent viscosity of at least 0.5 dL/g, heat of fusion of at least 10 J/g and capable of absorbing water at more than 10 percent (10%), of their dry mass when present in the biological environment, when said compositions are used as swellable surgical sutures, coatings of medical devices, and/or carriers for the delivery of bioactive agents. The crystalline amphiphilic compositions of the present invention comprise hydrophilic and hydrophobic components which can be covalently linked either directly or indirectly through an interlinking functionality such as a urethane group or flexible polymeric segment as a spacer. The hydrophilic component can be based on a crystalline polyether glycol, such as a polyethylene glycol, having a molecular weight of at least 5 kDa, an amorphous polyvinyl pyrrolidone glycol having a molecular weight of at least 10 kDa, partially neutralized, non-crystallizable, polyacrylic or polymethacrylic acid graft having a molecular weight of at least 2 kDa. On the other hand, the crystalline hydrophobic component can be comprised of (a) a polyester or copolyester chain, or (b) nylon 11, nylon 12, nylon 6, 10 chains, and alkylated derivatives thereof.

Another general aspect of this invention is directed to the use of the crystalline amphiphilic block/graft copolymers as swellable (a) surgical sutures capable of blocking tissue defects inflicted by the needle component of the suture, perioperatively, and hence, minimizing or eliminating blood leakage, particularly in surgeries associated with the cardiovascular system; (b) coatings for medical implants or devices where controlled expansion at a biological site is critical to the clinical efficacy of the device, as in the case of a space filling device associated with the treatment of aneurysms and particularly those of the vascular system; and (c) carriers for the delivery of bioactive agents where the release of these agents is controlled by time-dependent swelling profile of the carriers. The latter application is particularly valuable in the oral administration of single and multiple drugs where swelling in the stomach and intestine can be modulated by controlling the chemical structure of the carriers and their response to the acidic and basic environments, respectively. Another feature of the swellable carriers is the ability to change their density in the gastric fluid to control their residence time in the stomach.

This invention deals, in part, with structurally tailored, crystalline, amphiphilic, block copolymeric compositions comprising hydrophilic components such as those based on crystalline polyethylene glycol or amorphous polyvinyl pyrrolidone covalently linked either directly or indirectly through a flexible segment or a spacer to a crystalline hydrophobic component comprising repeat units derived from at least one of the cyclic monomers selected from a group represented by ε-caprolactone, p-dioxanone, glycolide, l-lactide, trimethylene carbonate, and a substituted or unsubstituted morpholinedione. The flexible segment or spacer interlinking the hydrophilic and hydrophobic components comprising repeat units derived from at least one of the cyclic monomers selected from the group represented by ε-caprolactone, trimethylene carbonate, and 1,5-dioxepan-2-one. The overall copolymeric composition is designed to display an inherent viscosity of at least 0.5 dL/g, minimum heat of fusion of 10 J/g, and absorb water for at least 10 percent (10%) of its original dry mass when present in the biological environment.

A specific aspect of this invention deals with crystalline amphiphilic block copolymers made by end-grafting a crystalline polyethylene glycol having a molecular weight of at least 5 kDa, preferably 10 kDa, more preferably 20 kDa, and most preferably 35 KDa with trimethylene carbonate or a mixture of trimethylene carbonate and ε-caprolactone to form flexible, terminal segments for further end-grafting to form the crystalline hydrophobic components. This can be based on at least one cyclic monomer selected from the group represented by glycolide, l-lactide, ε-caprolactone, p-dioxanone and a morpholinedione.

Another aspect of this invention deals with the (a) synthesis of a water-soluble or highly hydrophilic polyvinyl pyrrolidone or copolymer with one or more vinyl monomers form a macromolecular chain having one or two hydroxyl end-group, using a living free-radical polymerization protocol; (b) end-grafting the product from a with a trimethylene carbonate or mixture of ε-caprolactone to form a flexible spacer to interlink with the crystalline hydrophobic segment; and (c) end-grafting the product from a or b with at least one cyclic monomer selected from the group represented by glycolide, l-lactide, ε-caprolactone, p-dioxanone, a morpholinedione, and trimethylene carbonate.

A clinically important aspect of this invention pertains to the ability to modulate the rate of water absorption and the equilibrium water up-take of the copolymeric composition described in this invention. Accordingly, this invention deals with crystalline, amphiphilic, copolymeric block/graft compositions having controlled crosslink density wherein the crosslinking can be achieved by treating such composition with a mono- or polyfunctional vinyl monomer in the presence of a free-radical initiator or high-energy radiation. The crosslinking monomer can be introduced into the bulk of the amphiphilic composition by preswelling these compositions with a solution of the crosslinking agent and initiator, followed by drying under nitrogen. The dried composition can be heated or irradiated to achieve crosslinking.

A special aspect of this invention deals with crystalline amphiphilic block copolymeric compositions comprising a hydrophilic component made by interlinking a crystalline polyethylene glycol (PEG) with an organic diisocyanate at predetermined concentrations and under reaction conditions to yield urethane-interlinked PEG with at least one hydroxyl end-group. To form a typical amphiphilic composition, the urethane-interlinked PEG can be end-grafted with at least one cyclic monomer selected from the group represented by ε-caprolactone, p-dioxanone, glycolide, l-lactide, trimethylene carbonate, and a morpholinedione. When the resulting amphiphilic block copolymer is converted to a monofilament surgical suture, the swelling profile of the suture can be modulated by controlled crosslinking of the monofilament. A possible outcome of crosslinking is increasing the extent of swelling in the biological environment. The crosslinking can be achieved by diffusing a solution of a crosslinking agent into the bulk of the monofilament using a suitable organic solvent followed by drying and subsequent heating and/or irradiation with high-energy radiation in an inert atmosphere. Among other approaches for achieving the desired crosslinking are (a) reacting the urethane interlinking groups with an organic diisocyanate, and (b) acylating the urethane interlinking group with itaconic anhydride, followed by free-radical or radiation curing through the resulting itaconic acid double bond.

This invention is generally directed to a bioswellable, high molecular weight, crystalline, amphiphilic, block/graft copolymeric composition comprising a hydrophilic component covalently linked to a crystalline hydrophobic component wherein said composition exhibits an inherent viscosity of at least 0.5 dL/g, heat of fusion of at least 10 J/g and is capable of absorbing at least 10% of its dry mass of water when present in the biological environment, wherein both the hydrophilic and hydrophobic components are crystalline with the hydrophilic component comprising a polyethylene oxide central block and the hydrophobic component comprising two terminal blocks comprising repeat units arising from at least one cyclic monomer selected from the group represented by ε-caprolactone, p-dioxanone, glycolide, l-lactide, trimethylene carbonate, and a morpholinedione. Additionally, these compositions can be used clinically in the form of a swellable (a) surgical suture; (b) a coating for devices used in treating vascular aneurysm; and (c) a carrier for the delivery of at least one bioactive agent.

Another aspect of this invention deals with a bioswellable, high molecular weight, crystalline, amphiphilic, block/graft copolymeric composition comprising a hydrophilic component covalently linked to a crystalline hydrophobic component wherein said composition exhibits an inherent viscosity of at least 0.5 dL/g, heat of fusion of at least 10 J/g and is capable of absorbing at least 10% of its dry mass of water when present in the biological environment wherein the hydrophilic component is non-crystalline and the hydrophobic component is crystalline with the hydrophilic component comprising a polyvinyl pyrrolidone block/graft and the hydrophobic component comprising a polyester chain comprising repeat units arising from one or more cyclic monomer selected from the group represented by ε-caprolactone, p-dioxanone, glycolide, l-lactide, trimethylene carbonate, and a morpholinedione. Furthermore, these compositions can be used clinically in the form of surgical sutures, a coating for a medical device used in treating vascular aneurysm, and a carrier for the delivery of at least one bioactive agent.

Another aspect of this invention deals with a bioswellable, high molecular weight, crystalline, amphiphilic, block/graft copolymeric composition comprising a hydrophilic component covalently linked to a crystalline hydrophobic component wherein said composition exhibits an inherent viscosity of at least 0.5 dL/g, heat of fusion of at least 10 J/g and is capable of absorbing at least 10% of its dry mass of water when present in the biological environment, wherein both the hydrophilic and hydrophobic components are crystalline with the hydrophilic component comprising a polyethylene oxide central block and the hydrophobic component comprising two terminal blocks comprising repeat units arising from at least one cyclic monomer selected from the group represented by ε-caprolactone, p-dioxanone, glycolide, l-lactide, trimethylene carbonate, and a morpholinedione. It is preferred that the hydrophobic and hydrophilic components are interlinked through a flexible chain segment wherein the flexible chain segment comprising repeat units derive from at least one cyclic monomer selected from the group 1,5-dioxepane-2-one, trimethylene carbonate, and ε-caprolactone. Furthermore, these compositions can be used clinically in the form of a surgical suture, coating for a medical device used in treating vascular aneurysm, and carrier for the delivery of at least one bioactive agent.

A specific aspect of this invention deals with a bioswellable, high molecular weight, crystalline, amphiphilic, block/graft copolymeric composition comprising a hydrophilic component covalently linked to a crystalline hydrophobic component wherein said composition exhibits an inherent viscosity of at least 0.5 dL/g, heat of fusion of at least 10 J/g and is capable of absorbing at least 10% of its dry mass of water when present in the biological environment, wherein the hydrophilic component is non-crystalline and the hydrophobic component is crystalline with the hydrophilic component comprising a polyvinyl pyrrolidone block/graft and the hydrophobic component comprising a polyester chain comprising repeat units arising from one or more cyclic monomer selected from the group represented by ε-caprolactone, p-dioxanone, glycolide, l-lactide, trimethylene carbonate, and a morpholinedione. It is preferred that the hydrophobic and hydrophilic components are interlinked through a flexible chain segment. Furthermore, these compositions can be used clinically in the form of a carrier for the delivery of at least one bioactive agent.

A special aspect of this invention deals with the use of one or more of the bioswellable compositions described herein as gum bases for the formulation/production of biodegradable chewing gums. It is preferred that such gum base compositions are used as carriers for the delivery of one or more bioactive agent(s) including those commonly used in conjunction with oral hygiene and other orally administered drugs known to be effective in treating different diseases.

Further illustrations of the present invention are provided by the following examples:

Example 1

Preparation and Characterization of Crystalline Amphiphilic Triblock Block Copolymer Having a Central Polyethylene Oxide and Polyester Terminal Block (P-I Series): General Method Predried crystalline, high molecular weight PEG was mixed, under nitrogen in a stainless steel reactor equipped for mechanical stirring, with the desired amount(s) of cyclic monomer(s) in the presence of stannous octanoate as a catalyst. The mixture was then heated to achieve complete dissolution of all reactants. The mixing was continued while heating to a polymerization temperature of 160° C. The reaction was maintained at that temperature while stirring until the product became too viscous to stir and essentially complete monomer conversion was achieved (8-10 hours depending on the type and concentration of cyclic monomers). At this stage, polymerization was discontinued, the product was cooled, isolated, ground, dried, and traces of residual monomer was removed by distillation under reduced pressure using a temperature that is below the copolymer melting temperature ($T_m$), but not exceeding 110° C.

The resulting copolymer was characterized for (a) molecular weight in terms of inherent viscosity (I.V.) and $M_n/M_w$ by GPC if the polymer was soluble $CH_2Cl_2$; (b) $T_m$ and heat of fusion ($\Delta H_f$) using differential scanning calorimetry; (c) crystallinity using wide-angle X-ray diffraction.

Examples 2 to 16

Synthesis and Characterization of Specific Examples of Type P-I Block Copolymers (P-I-A to P-I-O)

Copolymers P-I-A to P-I-O were prepared and characterized following the general methods described in Example 1. The polymerization charge and properties of resulting polymers are summarized in Table I.

TABLE I

Synthesis and Properties of Copolymers P-I-A to P-I-O

| | | Composition of Charge | | | GPC[c] Data | | | DSC Data | |
|---|---|---|---|---|---|---|---|---|---|
| Polymer Number | PEG $M_n$, kD | PEG/Polyester, (wt) | Monomer Types & molar ratios[a] | Catalyst M/C[b] | Mn, kDa | Mw, kDa | IV[d] | Tm, ° C. | $\Delta H_f$, J/g |
| P-I-A | 20 | 10/90 | 90/10 LL/CL | 2500 | 52 | 94 | 0.8 | 174 | 40 |
| P-I-B | 35 | 10/90 | 90/10 LL/CL | 2000 | 59 | 107 | 1.5 | 175 | 35 |
| P-I-C | 35 | 15/85 | 90/10 LL/CL | 2000 | 38 | 73 | 1.1 | 152 | 32 |
| P-I-D | 35 | 50/50 | 90/10 LL/CL | 2000 | 19 | 35 | 0.7 | 60 | 87 |
| P-I-E | 35 | 40/60 | 85/15 LL/G | 2000 | 20 | 33 | 0.9 | 59 | 70 |
| P-I-F | 35 | 40/60 | 72/28 G/CL | 2000 | [e] | [e] | (1.2) | 45, 205 | 42, 47 |
| P-I-G | 20 | 50/50 | 65/35 DLL/G | 1500 | 19 | 30 | 0.6 | 56 | 86 |
| P-I-H | 20 | 10/90 | 90/10 LL/G | 2000 | 79 | 120 | 1.7 | 79, 156 | 21, 29 |
| P-I-I | 20 | 10/90 | 95/5 LL/CL | 2500 | 92 | 123 | 1.4 | 165 | 34 |
| P-I-J | 35 | 30/70 | 100 CL | 2000 | 38 | 92 | 1.3 | 73 | 103 |
| P-I-K | 35 | 30/70 | 97/3 LL/TMC | 2000 | 50 | 82 | 0.9 | 46, 154 | 4, 30 |
| P-I-L | 35 | 32/68 | 100 LL | 2000 | 66 | 140 | 1.0 | 49, 162 | 6, 35 |

TABLE I-continued

Synthesis and Properties of Copolymers P-I-A to P-I-O

| | Composition of Charge | | | | GPC[c] Data | | | DSC Data | |
|---|---|---|---|---|---|---|---|---|---|
| Polymer Number | PEG $M_n$, kD | PEG/Polyester, (wt) | Monomer Types & molar ratios[a] | Catalyst M/C[b] | Mn, kDa | Mw, kDa | IV[d] | Tm, °C. | $\Delta H_f$, J/g |
| P-I-M | 35 | 42/58 | 100 LL | 1200 | 64 | 103 | 0.8 | 60, 132 | 40, 18 |
| P-I-N | 35 | 35/65 | 100 CL | 1600 | 80 | 153 | 1.3 | 65 | 124 |
| P-I-O | 35 | 35/65 | 94/6 CL/LL | 1600 | 86 | 177 | 1.2 | 70 | 90 |

[a] G = Glycolide; LL = l-lactide; CL = ε-caprolactone; DLL = dl-lactide.
[b] Molar ratio of monomer to stannous octanoate.
[c] Gel permeation chromatography in $CH_2Cl_2$.
[d] Inherent viscosity in $CHCl_3$ (in HFIP).
[e] Insoluble in $CH_2Cl_2$.

Example 17

Preparation and Characterization of Crystalline Amphiphilic, Triblock Block Copolymers Having a Central Polyethylene Oxide Block Formed by the Interlinking of Polyethylene Glycol with an Organic Diisocyanate and Terminal Polyester Blocks (P-II Series): General Method The general polymerization methods and polymer isolation, purification, and characterization of P-II series were implemented using analogous experimental protocols as those described in Example 1 for the P-I series with the exception of the following:

The PEG was first interlinked using an organic diisocyanate at a 2:1 PEG:diisocyanate molar ratio at 130° C. The temperature was then raised to 140° C. and the monomeric precursor(s) of the crystalline hydrophobic component(s) was added and thoroughly mixed. The reaction temperature was then raised to 170° C. and polymerization was continued.

Example 18

Synthesis and Characterization of a Specific Example of Type P-II Block Polymer (P-II-A)

Copolymer P-II-A was prepared and characterized following the general methods described in Example 17. The polymerization charge and properties of the resulting polymer are summarized in Table II.

Example 19

Preparation and Characterization of Crystalline Amphiphilic Block Copolymer of Polyethylene Glycol (PEG) and Polyester Interlinked with Polytrimethylene Carbonate (PTMC) Segment (P-III Series): General Method The general polymerization methods and polymer isolation, purification, and characterization of P-III series were implemented using analogous experimental protocols as those described in Example 1 for the P-I series with the exception of the following:

The PEG was first end-grafted with trimethylene carbonate (TMC) at 150° C. until essentially complete monomer conversion was achieved. At this point, the temperature was lowered to 140° C. and the monomeric precursor(s) of the crystalline hydrophobic component(s) was added, thoroughly mixed with the PEG-PTMC copolymer. The reaction temperature was then raised to 160° C. or 170° C. depending on the type and concentration of cyclic monomer(s), and polymerization was continued.

Examples 20 to 24

Synthesis and Characterization of Specific Examples of Type P-II Block Copolymers (P-III-A to P-III-E)

Copolymers P-III-A to P-III-E were prepared and characterized following the general methods described in Example 19. Polymerization charge and properties of resulting polymers are summarized in Table III.

TABLE II

Synthesis and Properties of Copolymer P-II-A

| | Composition of Charge | | | GPC[c] Data | | DSC Data | |
|---|---|---|---|---|---|---|---|
| Polymer Number | PEG $M_n$, kD | PEG/Polyester, (wt) | Monomer Types & molar ratios[a] | Catalyst M/C[b] | Mn, kDa | Mw, kDa | Tm, °C. | $\Delta H_f$, J/g |
| P-II-A | 35 | 50/50 | 97/3 LL/TMC | 2000 | 25 | 48 | 59 | 78 |

[a] LL = l-lactide; TMC = trimethylene carbonate.
[b] Molar ratio of monomer to stannous octanoate.
[c] Gel permeation chromatography in $CH_2Cl_2$.

TABLE III

Synthesis and Properties of Copolymers P-III-A to P-III-E

| Polymer Number | Composition of Charge | | | Catalyst M/C[b] | GPC[c] Data | | IV[d] | DSC Data | |
|---|---|---|---|---|---|---|---|---|---|
| | PEG $M_n$, kD | PEG/TMC Polyester, (wt) | Monomer Types & molar ratios[a] | | Mn, kDa | Mw, kDa | | Tm, °C. | $\Delta H_f$, J/g |
| P-III-A | 35 | 25/15/60 | 88/12 LL/G | 2000 | 55 | 91 | 1.2 | 49, 141 | 13, 17 |
| P-III-B | 35 | 28/12/60 | 95/5 LL/G | 4000 | 44 | 74 | 1.1 | 51, 145 | 32, 31 |
| P-III-C | 35 | 31/9/60 | 95/5 LL/G | 4000 | 40 | 64 | 1.0 | 51, 127 | 42, 15 |
| P-III-D | 35 | 20/5/75 | 80/20 G/CL | 6000 | [e] | [e] | (1.4) | 47, 218 | 13, 56 |
| P-IIII-E | 35 | 25/2/73 | 83/17 G/TMC | 6000 | [e] | [e] | (1.2) | 44, 208 | 12, 50 |

[a]G = Glycolide; LL = l-lactide; CL = ε-caprolactone.
[b]Molar ratio of monomer to stannous octanoate.
[c]Gel permeation chromatography in $CH_2Cl_2$.
[d]Inherent viscosity in $CHCl_3$ (in HFIP).
[e]Insoluble in $CH_2Cl_2$.

Example 25

Melt-Spinning of Typical Block Copolymers and Suture Properties of Resulting Oriented Monofilaments The melt spinning of four typical block copolymers was accomplished using a ¾" extruder at the temperature noted in Table IV. The extrudates were oriented in two stages using the draw ratio/temperature recorded in Table IV.

TABLE IV

Extrusion and Processing Conditions of Typical Monofilaments

| Polymer | | Temperature Profile During extrusion, °C. @ | | | | Orientation Scheme Draw Ratio/Temp, °C. |
|---|---|---|---|---|---|---|
| No. | $T_m$ | Zone 1 | Zone 2 | Zone 3 | Spinhead | |
| P-I-C | 152 | 125 | 149 | 175 | 185 | 5–7 × @ 60 to 100 |
| P-II-A | 49, 141 | 65 | 135 | 160 | 166 | 9–18 × @ 70 to 95 |
| P-II-B | 51, 145 | 65 | 135 | 160 | 165 | 13–17 × @ 70–85 |
| P-II-C | 51, 127 | 80 | 110 | 130 | 145 | 14.8–15.6 × @ 60–70 |

Example 26

Properties of Typical Oriented Monofilaments as Swellable Sutures

The initial tensile properties, breaking strength retention (BSR) data of the monofilament sutures were determined using a MiniBionix MTS Universal Tester, Model 858. The simulated bioswelling properties were evaluated using a phosphate buffer at 37° C. and pH 7.4. The in vitro BSR data were determined on sutures incubated in a phosphate buffer at 37° C. and pH 7.4. Accumulated testing data are summarized in Table V.

TABLE V

Suture Properties of Typical Monofilaments

| Polymer Number | P-I-B | P-II-A | P-II-B | P-II-C |
|---|---|---|---|---|
| Physical Properties | | | | |
| Diameter, mm | 0.10 | 0.13 | 0.13 | 0.17 |
| Initial Strength, Kpsi | 73 | 46 | 45 | 23 |
| N | 3.66 | 4.2 | 4.0 | 3.57 |
| Modulus, Kpsi | 460 | 239 | 236 | 43 |
| Elongation, % | 54 | 44 | 85 | 95 |
| Knot Strength, N | 2.96 | 2.64 | — | 4.41 |
| Water Absorption/Swelling Data | | | | |
| Increase in Diameter, %/hour | — | 30.6/16 | 52.9/16 | 103.3/18 |
| Increase in volume, %/hour | — | 56.4/16 | 116/16 | 110.9/18 |
| In Vitro BSR, % @ Week 1 | 76 | 72 | — | — |
| Week 2 | 68 | — | 56 | — |
| Week 3 | 57 | — | — | — |

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A bioswellable, high molecular weight, crystalline, amphiphilic, block copolymeric composition comprising a crystalline hydrophilic component comprising polyethylene glycol having a molecular weight of at least 35 kDa, the crystalline hydrophilic component covalently linked to a crystalline hydrophobic polyester component via a flexible chain segment to form a pentablock copolymer, said crystalline hydrophobic component being a member selected from the group consisting of poly-l-lactide, polycaprolactone, and l-lactide copolymers with caprolactone, glycolide, or trimethylene carbonate in which l-lactide represents 90 to 95 mole %, the ratio of crystalline hydrophilic component to crystalline hydrophobic component being from 10/90 to 50/50 weight %, the composition exhibiting two distinct melting temperatures, having an inherent viscosity of at least 0.5 dL/g, heat of fusion of at least 10 J/g and is capable of absorbing at least 10% of its dry mass of water when present in the biological environment.

2. A bioswellable, high molecular weight, crystalline, amphiphilic, block copolymeric composition as set forth in claim 1 in the form of a surgical suture.

3. A bioswellable, high molecular weight, crystalline, amphiphilic, block/graft copolymeric composition as set forth in claim 1 in the form of a coating for devices used in treating vascular aneurysm.

4. A bioswellable, high molecular weight, crystalline, amphiphilic, block/graft copolymeric composition as set forth in claim 1 in the form of a carrier for the delivery of at least one bioactive agent.

5. A bioswellable, high molecular weight, crystalline, amphiphilic, block/graft copolymeric composition as set forth in claim 1 wherein the crystalline hydrophilic component is polyethylene glycol having a molecular weight of 35 kDa.

6. A bioswellable, high molecular weight, crystalline, amphiphilic, block/graft copolymeric composition as set forth in claim 5 wherein the crystalline hydrophobic component is a 90/10 mole % copolymer of l-lactide and caprolactone and the ratio of crystalline hydrophilic component to crystalline hydrophobic component is from 10/90 to 50/50 weight %.

7. A bioswellable, high molecular weight, crystalline, amphiphilic, block copolymeric composition comprising a crystalline hydrophilic component comprising polyethylene glycol having a molecular weight of at least 35 kDa, the crystalline hydrophilic component covalently linked to a crystalline hydrophobic polyester component via a flexible chain segment to form a pentablock copolymer, said crystalline hydrophobic component being a member selected from the group consisting of poly-l-lactide, polycaprolactone, or l-lactide copolymers with caprolactone, glycolide, trimethylene carbonate, or p-dioxanone the ratio of crystalline hydrophilic component to crystalline hydrophobic component being from 10/90 to 50/50 weight %, the composition exhibiting two distinct melting temperatures, having an inherent viscosity of at least 0.5 dL/g, heat of fusion of at least 10 J/g and is capable of absorbing at least 10% of its dry mass of water when present in the biological environment.

8. The bioswellable, high molecular weight, crystalline, amphiphilic, block copolymeric composition of claim 7 wherein the flexible chain segment comprises at least one cyclic monomer selected from the group consisting of ε-caprolactone, 1,5-dioxepane-2-one, trimethylene carbonate, or mixtures thereof.

9. The bioswellable, high molecular weight, crystalline, amphiphilic, block copolymeric composition of claim 7 in the form of a surgical suture, coating for a medical device, or carrier for the delivery of at least one bioactive agent.

10. A crystalline, amphiphilic, block copolymeric composition comprising:
   a crystalline hydrophilic component having a molecular weight of at least 35 kDa;
   the crystalline hydrophilic component end-grafted to at least one cyclic monomer to form a triblock polymer;
   a crystalline hydrophobic polyester component covalently bonded to the at least one cyclic monomer to form a pentablock copolymer;
   the crystalline hydrophobic component comprising repeat units from at least one cyclic monomer selected from the group consisting of caprolactone, glycolide, l-lactide, trimethylene carbonate, p-dioxanone, or mixtures thereof;
   the ratio of crystalline hydrophilic component to crystalline hydrophobic component being from 10/90 to 50/50 weight %; and
   the composition capable of absorbing at least 10% of its dry mass of water when present in the biological environment.

* * * * *